(12) United States Patent
Inoue et al.

(10) Patent No.: US 10,835,222 B2
(45) Date of Patent: Nov. 17, 2020

(54) METHOD FOR TREATING GASTRO ESOPHAGEAL REFLUX DISEASE

(71) Applicant: OLYMPUS CORPORATION, Hachioji (JP)

(72) Inventors: Haruhiro Inoue, Tokyo (JP); Kunihide Kaji, Tokyo (JP); Yuji Kishimoto, Tokyo (JP); Yoshie Aikawa, Tokyo (JP); Nobuko Matsuo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/279,381

(22) Filed: Feb. 19, 2019

(65) Prior Publication Data

US 2020/0261069 A1    Aug. 20, 2020

(51) Int. Cl.
| | | |
|---|---|---|
| *A61B 17/00* | (2006.01) | |
| *A61B 18/14* | (2006.01) | |
| *A61B 18/00* | (2006.01) | |

(52) U.S. Cl.
CPC .... *A61B 17/00234* (2013.01); *A61B 18/1492* (2013.01); *A61B 2017/00269* (2013.01); *A61B 2017/00827* (2013.01); *A61B 2018/00482* (2013.01); *A61B 2018/00494* (2013.01); *A61B 2018/00577* (2013.01)

(58) Field of Classification Search
CPC .... A61B 17/00234; A61B 2017/00269; A61B 2017/00827; A61B 2018/00494
See application file for complete search history.

(56) References Cited

U.S. PATENT DOCUMENTS 9,119,622 B2 *   9/2015   Rahmani .......... A61B 17/12013
9,592,070 B2      3/2017   Inoue
2017/0312029 A1 * 11/2017  Schaer ................ A61B 8/4281

* cited by examiner

*Primary Examiner* — William H Matthews
(74) *Attorney, Agent, or Firm* — Oliff PLC

(57) ABSTRACT

In an endoscopic treatment method, a damaged area is formed in at least a portion of a digestive tract along a circumferential direction. The damaged area is formed by performing thermal ablation of mucosal layer and not removing the mucosal layer. An incomplete stenosis is formed in the digestive tract during restoration of the damaged area.

15 Claims, 6 Drawing Sheets

METHOD FOR TREATING GASTRO ESOPHAGEAL REFLUX DISEASE

BACKGROUND

Two types of possible treatments for gastro esophageal reflux disease (GERD) are (1) an oral treatment with a gastric acid secretion inhibitor, and (2) a surgical treatment such as laparoscopic Nissen fundoplication.

Oral treatment requires administration for a long time, and symptoms may not improve.

Surgical treatment can be solve the problem but is highly invasive. Since GERD is not a malignant disease such as a tumor, it is desirable that the treatment be minimally invasive.

A variety of endoscopic treatments are considered as options other than oral and surgical treatments. A procedure described in U.S. Pat. No. 9,592,070 is known as one of endoscopic treatments. In this procedure, the mucous membrane in the vicinity of the gastroesophageal junction is resected to cause scarring at the resected site and cause stenosis. As a result, reflux of stomach contents is suppressed.

SUMMARY

An exemplary embodiment of an endoscopic treatment method, in which a damaged area is formed in at least a portion of a digestive tract along a circumferential direction, involves the damaged area being formed by performing thermal ablation of mucosal layer while maintaining the mucosal layer, and an incomplete stenosis being formed in the digestive tract during restoration of the damaged area.

DETAILED DESCRIPTION OF THE EMBODIMENTS

When performing an endoscopic treatment method for gastro esophageal reflux disease according to the present embodiment (hereinafter, simply referred to as "treatment method"), the operator first inserts an endoscope through a natural opening such as mouth or nose of the subject (insertion step), and moves the distal end of the endoscope into the stomach (digestive tract). As the endoscope, a known flexible endoscope can be used.

Figure 1:
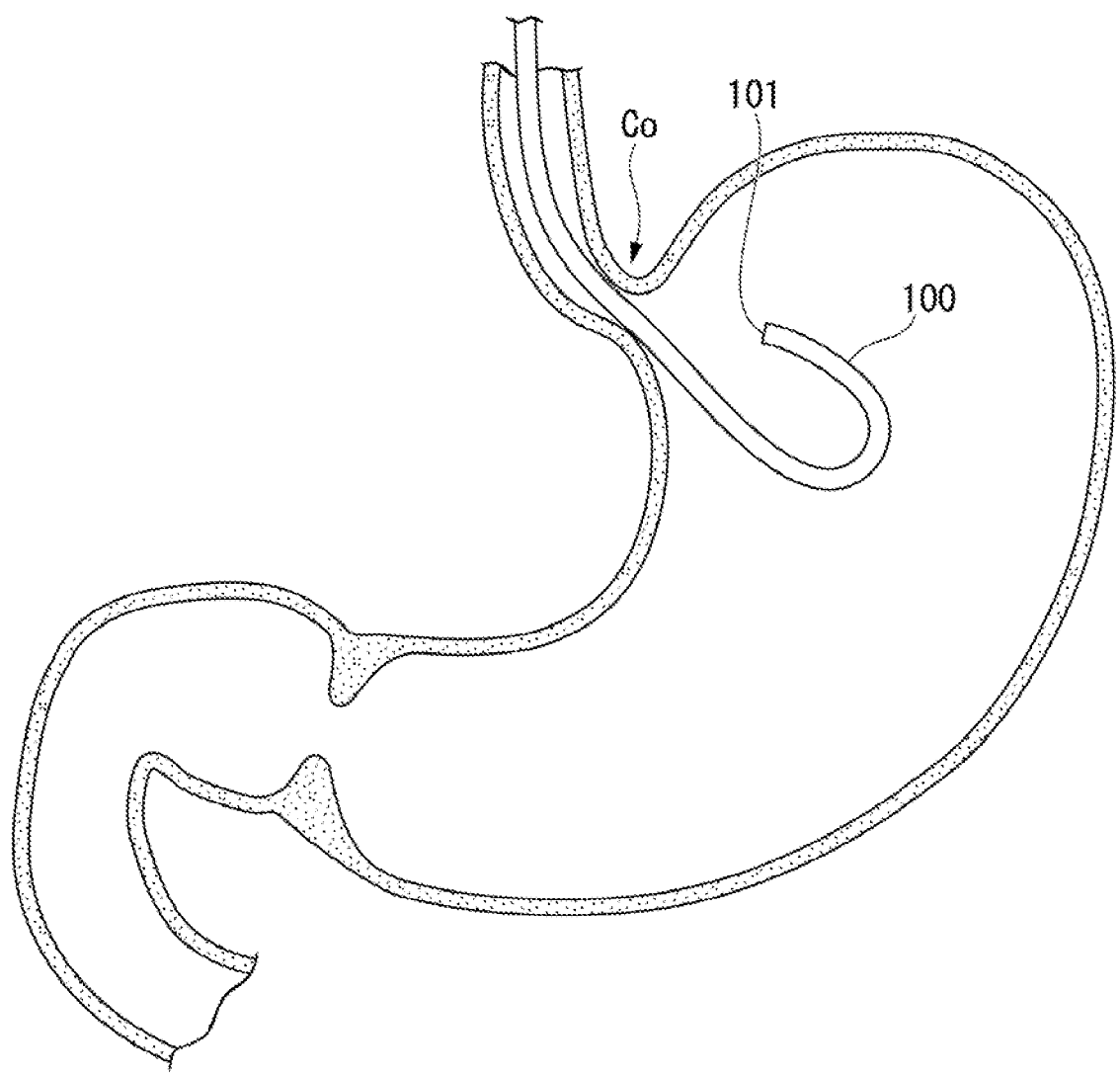
FIG. 1 is a view showing a state in which a gastroesophageal junction is observed with an endoscope inserted in the stomach.

Next, the operator operates the endoscope 100 to bend it. As shown in FIG. 1, the operator directs the distal end 101 of the endoscope 100 to the cardiac orifice Co, and captures the gastroesophageal junction around the cardiac orifice Co within the field of view of the endoscope 100. While observing the gastroesophageal junction, the operator determines a treatment area to be subjected to the thermal ablation treatment described later (step A).

Figure 2:
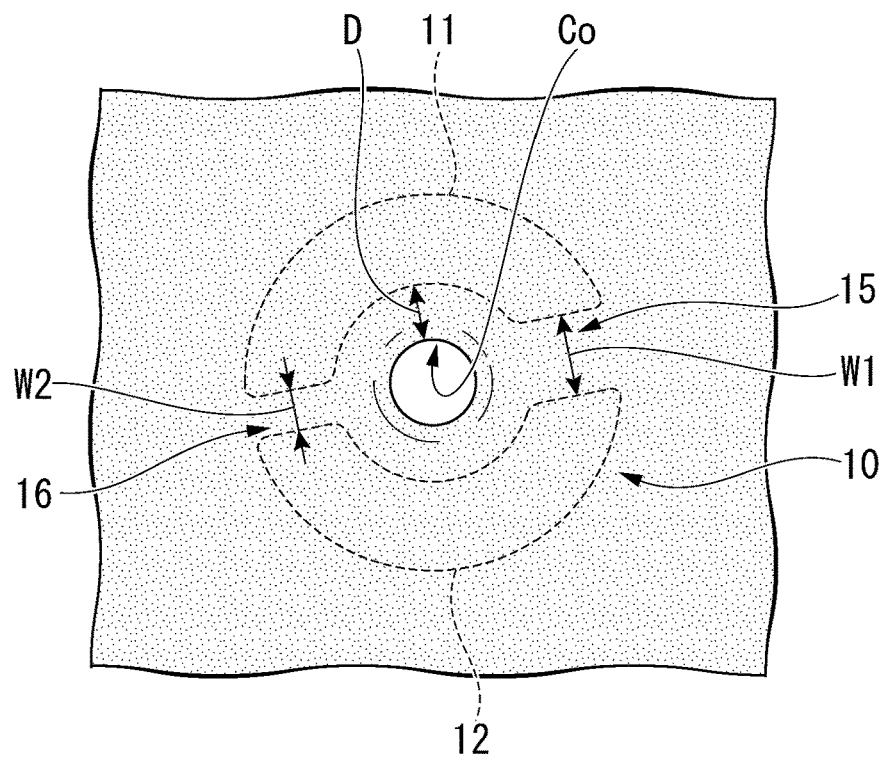
FIG. 2 is a view showing an example of a treatment area.

FIG. 2 shows an example of the treatment area. As shown in FIG. 2, the treatment area 10 has a shape in which a first area 11 and a second area 12 which are C-shaped or U-shaped face each other with a cardiac orifice Co interposed therebetween. The first area 11 is located on the anterior wall side of the stomach. The second area 12 is located on the posterior wall side of the stomach. The first area 11 and the second area 12 extend in the circumferential direction of the gastroesophageal junction.

By arranging the two sub-areas of the first area 11 and the second area 12 opposite to each other, the first boundary portion (first non-damaged area) 15 is located on the greater curvature side and the second boundary portion (second non-damaged area) 16 are located on the lesser curvature side, respectively. The first boundary portion 15 extends along the greater curvature. The second boundary 16 extends along the lesser curvature.

The width W1 of the first boundary portion 15 (the dimension in the circumferential direction of the gastroesophageal junction) is larger than the width W2 of the second boundary portion 16. For example, the width W1 is 10 to 20 millimeters, and the width W2 is 5 to 10 millimeters. In the following description, the first area 11 and the second area 12 may be collectively referred to as "sub-areas 11 and 12".

The sub-areas 11 and 12 are respectively separated from the cardiac orifice Co by a predetermined distance D. The predetermined distance D is, for example, 5 to 10 millimeters. The predetermined distance D of the first area 11 and the predetermined distance D of the second area 12 may not be the same.

The width of the sub-areas 11 and 12 extending in an arcuate shape along the circumferential direction of the gastroesophageal junction is, for example, 10 to 20 mm. The width may be constant or may vary depending on the site. Furthermore, the width of the first area 11 and the width of the second area 12 may be different.

Figure 3:
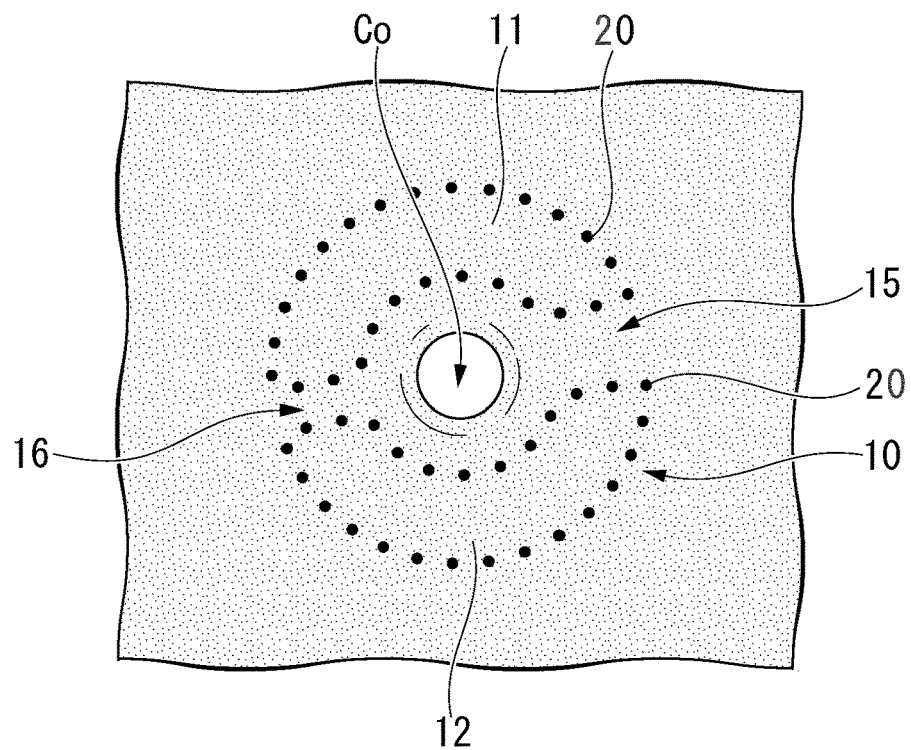
FIG. 3 is a view showing an example of a treatment area in which a marking is formed.

Next, the operator causes the treatment tool to protrude from the endoscope, and forms markings 20 around the treatment area 10 determined as shown in FIG. 3 using the treatment tool (step B). The markings 20 are formed by locally performing thermal ablation of the mucous membrane at the peripheral portions of the sub-areas 11 and 12. As a treatment tool for forming the markings 20, for example, a high frequency knife or a heat probe can be used.

The markings 20 need not be formed all around the treatment area, but may be formed at a plurality of spaced apart locations. In the treatment method of the present embodiment, since the first boundary portion 105 and the second boundary portion 106 play an important role, the markings 20 may be provided only around the first boundary portion 105 and the second boundary portion 106.

Figure 4:
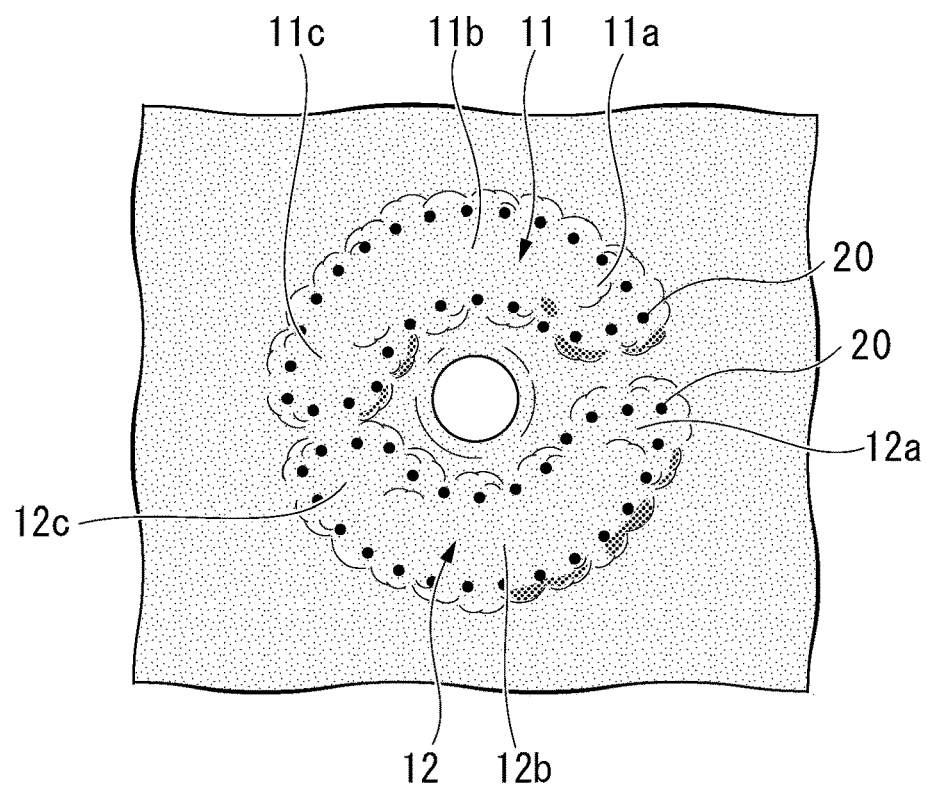
FIG. 4 is a view showing an example of a treatment area that is swollen.

Next, the operator injects a liquid into the submucosal layer of each of the sub-areas 11 and 12 to swell and expand each of the sub-areas 11 and 12 as shown in FIG. 4 (step C).

Saline solution or the like can be used as a liquid to inject. Since the degree of thermal ablation can be easily grasped in a later step, it is preferable to color the liquid with a dye used in gastroscopes such as indigo blue or the like. The liquid can be injected using a local injection needle or the like for an endoscope.

When an endoscope having a plurality of treatment tool channels is used in step C, replacement work of the treatment tool can be omitted by passing the local injection needle or the like and the treatment tool used for marking through different treatment tool channels.

Figure 10:
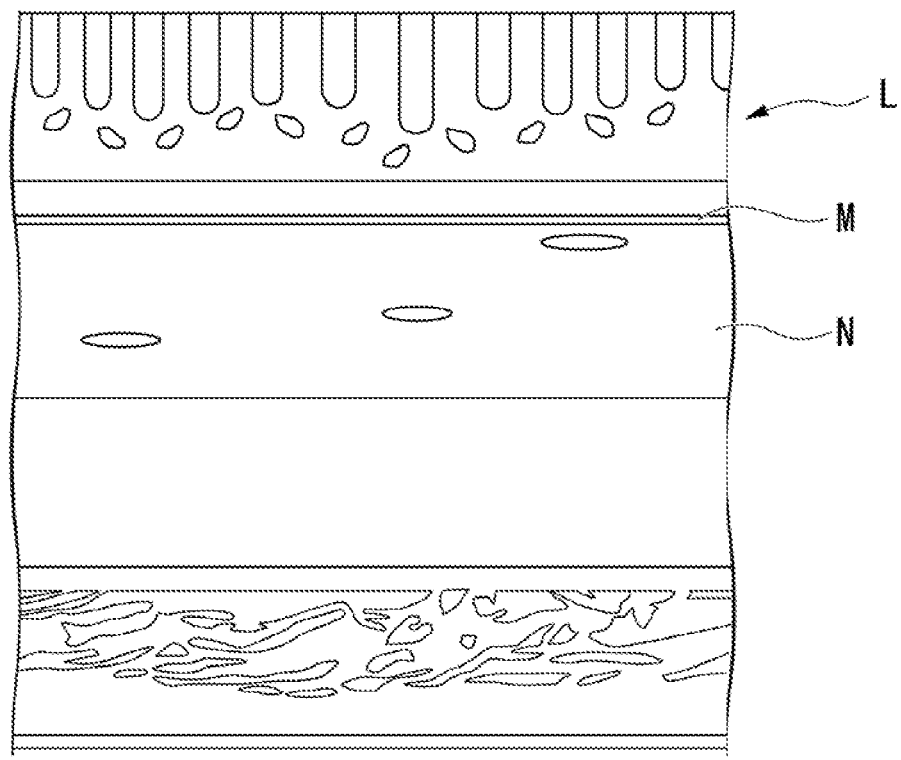
FIG. 10 is a schematic cross-sectional view of a stomach wall.

Next, the operator uses the treatment tool protruded from the endoscope to perform thermal ablation of the portions 11a and 12a (see FIG. 4) which are close to the greater curvature side of the gastric mucosa in the sub-areas 11 and 12. The thermal ablation is performed without excising the mucous membrane. The degree of thermal ablation is such that the mucosal base layer is damaged. FIG. 10 shows a schematic cross-sectional view of the stomach wall. The mucosal base layer M is a part of the mucosal layer L and is a layer that includes an interface in contact with the submucosal layer N. It is also called basement membrane.

The portions 11a and 12a that are swollen have a positional relationship that makes it easy to face the endoscope due to the anatomical shape of the stomach bottom.

Figure 5:
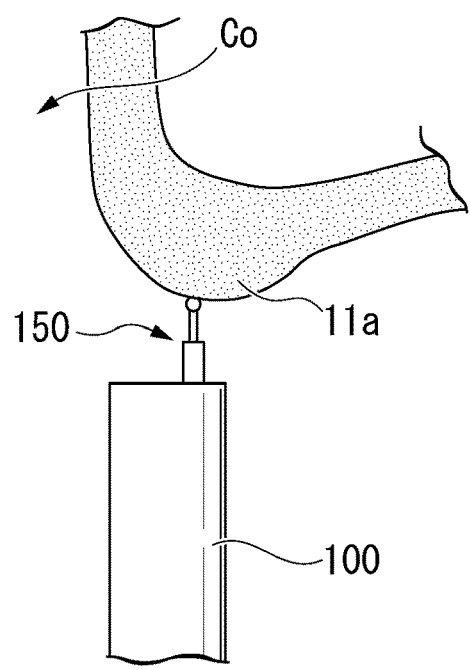
FIG. 5 is a view showing a state in which a treatment tool protruded from an endoscope is in contact with a portion close to a greater curvature side of the treatment area.

Thereby, by advancing the treatment tool 150 while fixing the endoscope 100, the treatment tool 150 can be brought into contact with the mucous membrane of the target portions 11a and 12a as shown in FIG. 5.

When a high-frequency knife is used as the treatment tool 150, the treatment tool 150 may be retracted little by little without moving the endoscope 100 from the state shown in FIG. 5 in which the distal end of the treatment tool 150 of which power supply is set to a coagulation mode is lightly pressed on the mucous membrane, and the thermal ablation may be performed at the timing when the distal end is separated from the mucous membrane. When treated according to such a procedure, the discharge from the distal end can be used to suitably perform thermal ablation of the mucous membrane. This is an example of a thermal ablation procedure, and thermal ablation may be performed in other procedures.

The operator performs thermal ablation of the entire mucous membrane in the portions 11a and 12a by repeating thermal ablation while twisting or bending the endoscope 100 to change the position of the distal end of the treatment tool 150. Since the portions 11a and 12a are close to the stomach bottom, this step performs thermal ablation of the area on the stomach bottom side of the treatment area 10.

Next, the operator uses the treatment tool protruded from the endoscope to perform thermal ablation of the portions 11b and 12b closer to the anterior and posterior walls and the portions 11c and 12c (see FIG. 4) closer to the lesser curvature side of the gastric mucosa in the sub-areas 11 and 12. Also in this case, it should be noted that only thermal ablation is performed without excising the mucous membrane. The treatment tool to be used may be the same as thermal ablation of the portions 11a and 12a.

The portions 11b, 12b and 11c, 12c are difficult to face the endoscope 100 even if they are swollen due to the anatomical shape of the stomach. As a result, the treatment tool 150 protruding from the endoscope 100 approaches the mucous membrane in a state parallel or nearly parallel to the stomach wall.

Figure 6:
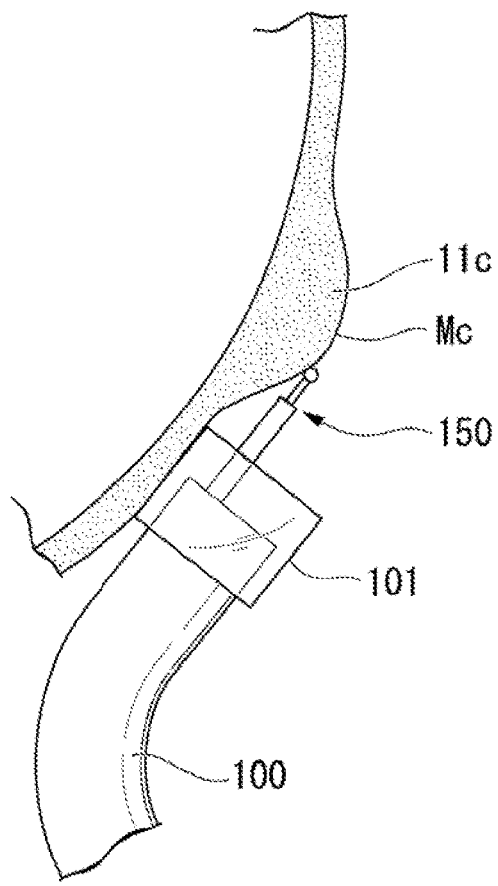
FIG. 6 is a view showing a state in which a treatment tool protruded from an endoscope is in contact with a portion close to a lesser curvature side of the treatment area.

Therefore, when using a high-frequency knife as the treatment tool 150, the treatment tool 150 is advanced along the mucous membrane Mc with the endoscope 100 fixed along the stomach wall as shown in FIG. 6, and thermal ablation may be performed while retracting the treatment tool 150. When treatment is performed according to such a procedure, it is possible to suitably perform thermal ablation of the mucous membrane using the discharge from the distal end of the treatment tool 150. This is an example of the thermal ablation procedure, and thermal ablation may be performed in other procedures. In FIG. 6, the cap 101 is attached to the distal end of the endoscope 100. Although the attachment of the cap 101 is not essential, the attachment of the cap allows the stomach wall to be pushed while maintaining a good view of the endoscope. As a result, the treatment instrument can be brought closer to the mucous membrane.

When thermal ablation of the entire mucosal layer in the treatment area 10 is ended, the treatment area 10 becomes a damaged area where thermal ablation is performed while the mucosal layer remains. The operator removes the endoscope and ends the procedure. After thermal ablation, the entire treatment area may be observed with an endoscope and additional thermal ablation may be performed according to the observation result.

Figure 7:
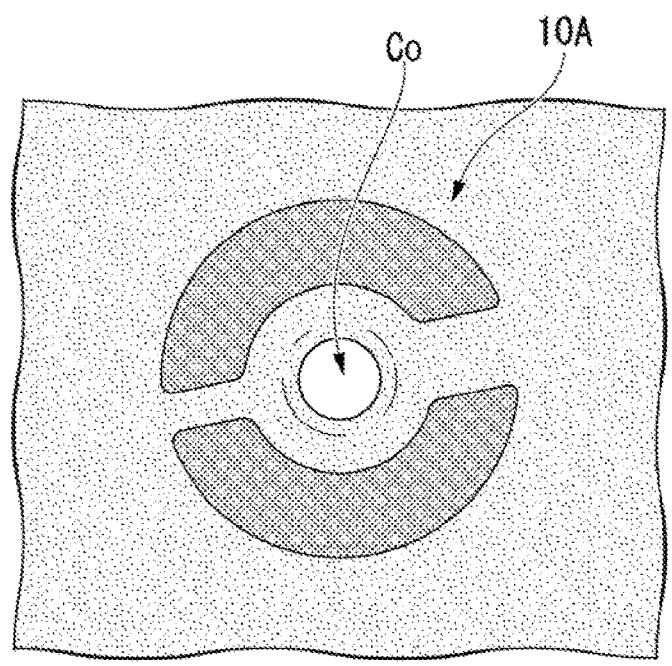
FIG. 7 is a diagram showing an example of the damaged area.

An example of the damaged area 10A after thermal ablation is shown in FIG. 7. The mucosal layer in the damaged area 10A remains because it has not been excised. The gastric mucosa in the damaged area 10A is damaged to reach the mucosal base layer by thermal ablation, and thereafter is regenerated through scarring. During regeneration of the mucous membrane, the gastric mucosa around the treatment area is drawn toward the treatment area by the reduction of the scar formed at the thermal ablation site. As a result, the gastric mucosa is bent at the first boundary portion 15 and the second boundary portion 16, and as shown in FIG. 8, the protruding pleats 111 and 112 extend in the circumferential direction of the gastroesophageal junction.

Figure 8:
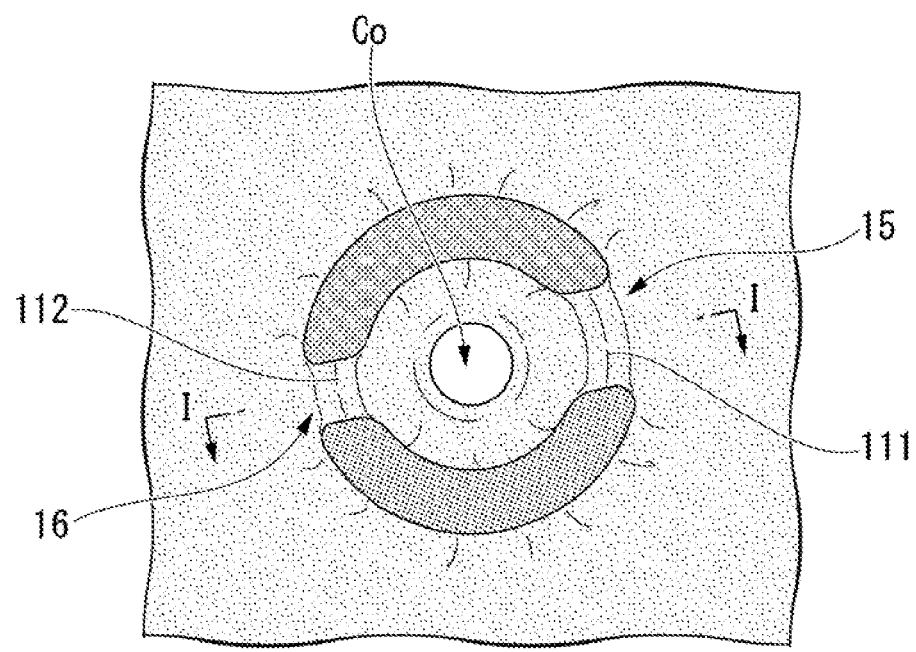
FIG. 8 is a view showing an example of an incomplete stenosis formed along with the restoration of the damaged area.
Figure 9:
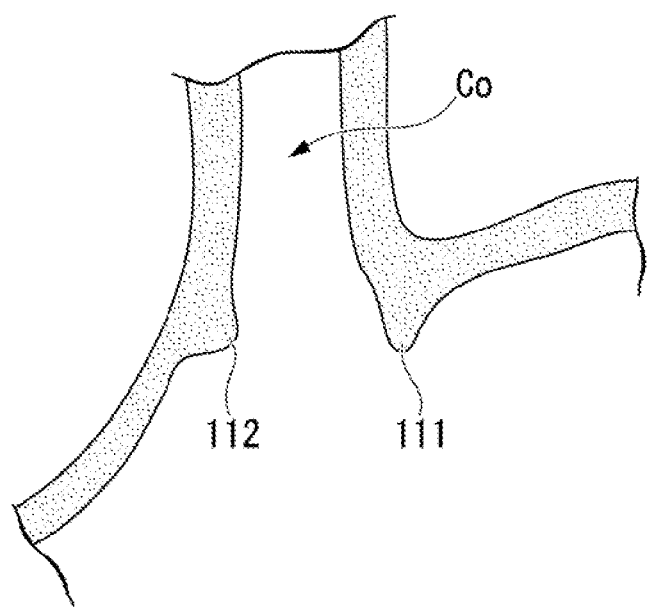
FIG. 9 is a cross-sectional view taken along the line I-I of FIG. 8.

FIG. 9 shows a schematic cross-sectional view taken along line I-I of FIG. 8. The pleats 111 form a His angle on the greater curvature side. The pleats 112 function as a valve to prevent backflow from the lesser curvature side. In the subject on which the treatment method is applied, incomplete stenosis is formed in the cardiac orifice by the pleats 111 and 112. As a result, reflux of the gastric contents is reduced and the symptoms of GERD are ameliorated.

As described above, the treatment method of the present embodiment can be performed simply by performing thermal ablation of the treatment area 10 using the endoscope 100 and the treatment tool 150 inserted from the natural opening, so it is easy to perform. The treatment method of the present embodiment can be performed only by bringing the distal end of the treatment tool 150 close to the mucous membrane, so the degree of difficulty of the procedure is low.

In addition, since thermal ablation of the tissue in the stomach is performed and thermal ablation of the esophagus is not performed, discomfort or the like at the time of swallowing due to a strong constriction in the esophagus is hard to occur.

The treatment method of the present embodiment can be implemented simply by bringing the treatment tool close to the mucous membrane to perform thermal ablation, so it is easy to perform thermal ablation of the operator's intended range.

In the procedure for excising the mucous membrane, if the therapeutic effect of GERD is not sufficient due to the form of scarring after excision or the like, it is difficult to perform the same treatment again on the site from which the mucous membrane was excised.

On the other hand, although the treatment method of the present embodiment damages the mucous membrane, it remains without excision, and therefore, it can be applied to a portion where the mucous membrane excision is difficult due to tissue fibrosis and the like. In the endoscopic observation of incomplete stenosis after a predetermined period of time, if the formation of the folds 111, 112, or the like is not sufficient, thermal ablation can be performed again on the mucosal layer (step D). Therefore, it is possible to flexibly respond to retreatment or additional treatment according to the follow-up result.

Various parameters such as the shape, size, and degree of damage of the treatment area related to thermal ablation after the follow-up may be the same as or different from the first treatment.

The treatment method of the present embodiment uses high-frequency coagulation developed for hemostasis as a treatment principle, so there is almost no risk of perforation of the stomach wall or bleeding after treatment. In the treatment method of the present embodiment, strict control of the injection amount of liquid for swelling and expanding strictly controlled by a conventional procedure, the amount of air supplied into the stomach, or the like is not required, and this point is also simple.

In the treatment area 10, in addition to the first boundary portion 105 forming the His angle, the second boundary 106 exists as an undamaged area between the sub-areas 11 and 12. As a result, excessive narrowing is less likely to occur in the treatment area than in the case where the treatment area is annular or is a single area with a long extension.

As described above, although an embodiment was described, the technical scope is not limited to the the above embodiment. In the range which does not deviate from the scope of exemplary embodiments, it is possible to change the combination of components, make various changes to or delete each component. Although some modifications are illustrated below, these are not all, and other modifications are possible. Two or more of these changes may be combined as appropriate.

In the treatment method of the present embodiment, the order which performs thermal ablation of a treatment area can be changed suitably. For example, thermal ablation of portions 11a, 11b, and 11c may be performed in any order. Alternatively, thermal ablation of the first area 11 and the second area 12 may be performed in parallel, or thermal ablation of one of the first area 11 and the second area 12 may be performed before thermal ablation of the other is performed.

Since the thermal ablation in the treatment method of the present embodiment does not reach a muscle layer, the treatment method of the present embodiment can be performed even if swelling does not occur. That is, step C may be omitted.

The digestive tract used as the object of the treatment method of the present embodiment is not restricted to a stomach, and it is applicable also to esophagus or the like. For example, when the subject to be treated has symptoms of esophageal mucosal hypersensitivity, or the like, part or all of the treatment area may be located in the esophagus.

When the treatment area is set in the esophagus, if the treatment is performed over the entire area of a certain area with no gap in the circumferential direction, excessive stenosis may occur. The possibility of causing excessive stenosis can be reduced by methods such as providing a non-treatment area in a circumferential direction, providing a non-treatment area in a helical shape, or providing a non-treatment area intermittently in the axial direction.

Moreover, the treatment method of the present embodiment is not only treatment of GERD which is dysfunction of esophagus, but can be applied to treatment of dysfunction of sphincter in other parts of digestive tract (for example, fecal incontinence which is dysfunction of anal sphincter, or the like).

What is claimed is:

1. An endoscopic treatment method comprising:
    forming a damaged area in at least a portion of a digestive tract along a circumferential direction by performing thermal ablation while keeping a mucosal layer; and
    forming an incomplete stenosis in the digestive tract, while restoring the damaged area,
    wherein the damaged area is formed by causing damage to a mucosal base layer, the mucosal base layer having an interface that contacts a submucosal layer.

2. The endoscopic treatment method according to claim 1, wherein
    the digestive tract is a stomach;
    the damaged area includes the mucosal layer of an inner wall of the stomach near a cardiac orifice;
    a gap is provided between the damaged area and the cardiac orifice; and
    the incomplete stenosis is formed around the cardiac orifice.

3. The endoscopic treatment method according to claim 2, wherein
    the damaged area is formed only in the portion along the circumferential direction of the stomach.

4. The endoscopic treatment method according to claim 3, wherein
    the damaged area includes:
        an arcuate first area formed at an anterior wall of the stomach; and
        an arcuate second area formed at a posterior wall of the stomach, wherein:
    a first non-damaged area is positioned between the first area and the second area, and on a greater curvature side, the first non-damaged area being a first area where thermal ablation of the mucosal layer is not performed,
    a second non-damaged area is positioned between the first area and the second area, and on a lesser curvature side, the second non-damaged area being a second area where thermal ablation of the mucosal layer is not performed, and
    a dimension of the first non-damaged area in the circumferential direction is greater than a dimension of the second non-damaged area in the circumferential direction.

5. The endoscopic treatment method according to claim 2, further comprising:
    before performing thermal ablation of the mucosal layer, observing a junction between the stomach and esophagus with an endoscope inserted into the stomach, and identifying a treatment area to form the damaged area; and
    forming a marking on at least a portion of a periphery of the treatment area.

6. The endoscopic treatment method according to claim 5, further comprising:
    after forming the marking, infusing liquid into a submucosa of the treatment area to swell the treatment area.

7. The endoscopic treatment method according to claim 1, further comprising:

observing a condition of the incomplete stenosis generated in the digestive tract and additionally performing thermal ablation of the mucosal layer according to a result of the observation.

8. The endoscopic treatment method according to claim 1, wherein the mucosal layer is not excised.

9. An endoscopic treatment method comprising:
forming a damaged area in at least a portion of a digestive tract along a circumferential direction by performing thermal ablation while keeping a mucosal layer; and
forming an incomplete stenosis in the digestive tract, while restoring the damaged area,
wherein the digestive tract is a stomach,
the damaged area includes the mucosal layer of an inner wall of the stomach near a cardiac orifice,
the incomplete stenosis is formed around the cardiac orifice,
the damaged area includes:
an arcuate first area formed at an anterior wall of the stomach; and
an arcuate second area formed at a posterior wall of the stomach, wherein:
a first non-damaged area is positioned between the first area and the second area, and on a greater curvature side, the first non-damaged area being a first area where thermal ablation of the mucosal layer is not performed,
a second non-damaged area is positioned between the first area and the second area, and on a lesser curvature side, the second non-damaged area being a second area where thermal ablation of the mucosal layer is not performed, and
a dimension of the first non-damaged area in the circumferential direction is greater than a dimension of the second non-damaged area in the circumferential direction.

10. The endoscopic treatment method according to claim 9, further comprising:
a first portion of at least one of the first area and the second area; and
a second portion of at least one of the first area and the second area,
wherein the first portion is closer to a greater curvature side than the second portion, and
thermal ablation of the first portion is performed before thermal ablation of the second portion.

11. The endoscopic treatment method according to claim 9, wherein a gap is provided between the damaged area and the cardiac orifice.

12. The endoscopic treatment method according to claim 9, wherein the damaged area is formed only in the portion along the circumferential direction of the stomach.

13. The endoscopic treatment method according to claim 9, further comprising:
before performing thermal ablation of the mucosal layer:
observing a junction between the stomach and esophagus with an endoscope inserted into the stomach, and identifying a treatment area to form the damaged area; and
forming a marking on at least a portion of a periphery of the treatment area.

14. The endoscopic treatment method according to claim 13, further comprising:
after forming the marking, infusing liquid into a submucosa of the treatment area to swell and lift up the treatment area.

15. The endoscopic treatment method according to claim 9, further comprising:
observing a condition of the incomplete stenosis generated in the digestive tract and additionally performing thermal ablation of the mucosal layer according to a result of the observation.

* * * * *